(12) United States Patent
Leavell

(10) Patent No.: US 8,414,353 B1
(45) Date of Patent: Apr. 9, 2013

(54) BRASSIERE CONFIGURED TO RECEIVE BREAST PUMP RECEPTACLE

(76) Inventor: Ashley Leavell, Rockmart, GA (US)

(*) Notice: Subject to any disclaimer, the term of this patent is extended or adjusted under 35 U.S.C. 154(b) by 203 days.

(21) Appl. No.: 12/954,696

(22) Filed: Nov. 26, 2010

(51) Int. Cl.
*A41C 3/00* (2006.01)

(52) U.S. Cl.
USPC ............................................. 450/36; 604/89

(58) Field of Classification Search .............. 450/36, 450/37, 54–58, 89
See application file for complete search history.

(56) References Cited

U.S. PATENT DOCUMENTS

| | | | |
|---|---|---|---|
| 5,514,166 A * | 5/1996 | Silver et al. | 604/74 |
| 5,571,084 A * | 11/1996 | Palmer | 604/74 |
| 5,575,768 A * | 11/1996 | Lockridge et al. | 604/74 |
| 5,611,086 A * | 3/1997 | Eggen | 2/104 |
| 6,004,186 A * | 12/1999 | Penny | 450/36 |
| 6,027,396 A * | 2/2000 | Yonchar | 450/36 |
| 6,032,289 A * | 3/2000 | Villapiano | 2/102 |
| 6,213,840 B1 * | 4/2001 | Han | 450/36 |
| 6,227,936 B1 * | 5/2001 | Mendoza | 450/36 |
| 6,247,996 B1 * | 6/2001 | Fields | 450/36 |
| 6,440,100 B1 * | 8/2002 | Prentiss | 604/74 |
| 6,659,841 B2 * | 12/2003 | Raimondo | 450/36 |
| 6,887,217 B1 * | 5/2005 | Logan | 604/74 |
| 6,974,361 B2 * | 12/2005 | Cravaack et al. | 450/36 |
| 7,094,217 B2 * | 8/2006 | Fialkoff | 604/74 |
| 7,559,915 B2 * | 7/2009 | Dao et al. | 604/74 |
| 7,611,399 B2 * | 11/2009 | Brigham | 450/36 |
| 8,057,452 B2 * | 11/2011 | Fialkoff | 604/385.07 |
| 8,137,153 B2 * | 3/2012 | Bell | 450/36 |

\* cited by examiner

*Primary Examiner* — Gloria Hale
(74) *Attorney, Agent, or Firm* — Gulf Coast Intellectual Property Group

(57) ABSTRACT

A bra configured to assist a user in providing support for at least a portion of the components of a breast pump during the milk extraction process. The bra further includes a stretchable strap that circumferentially surrounds the user's torso. Integrally formed with the strap are a pair of bra cups. The bra cups have an aperture centrally located that is in general alignment with the user's nipple and areola portion of the breast disposed within the bra cups. The bra cups are releasably secured proximate their top portion and are configured to fold in a downward direction so as to allow a user to place the conical shaped portion of a breast pump adjacent to the breast. A bottle support member is secured to the stretchable strap and can be deployed so as to provide substantial support for the milk receptacle of a conventional breast pump so as to minimize the requirement for the user to hold the breast pump components during milk extraction.

19 Claims, 3 Drawing Sheets

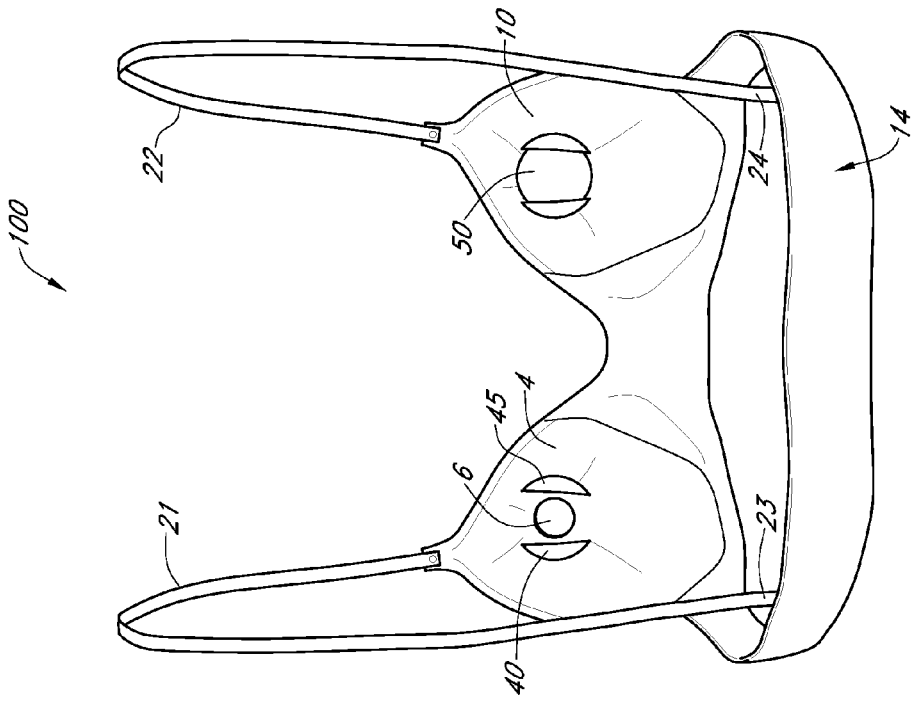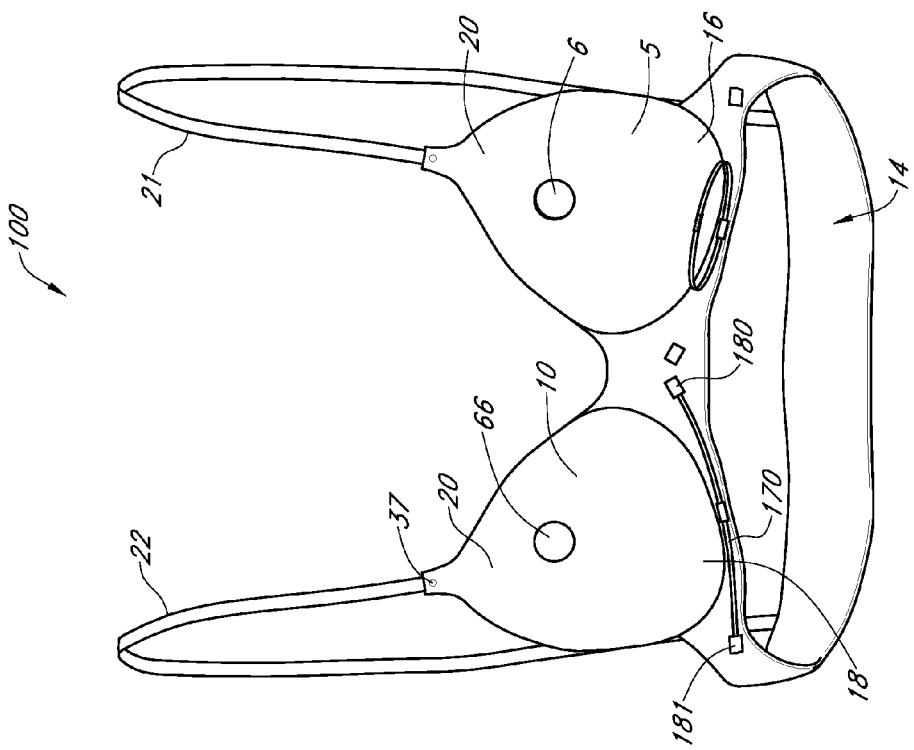

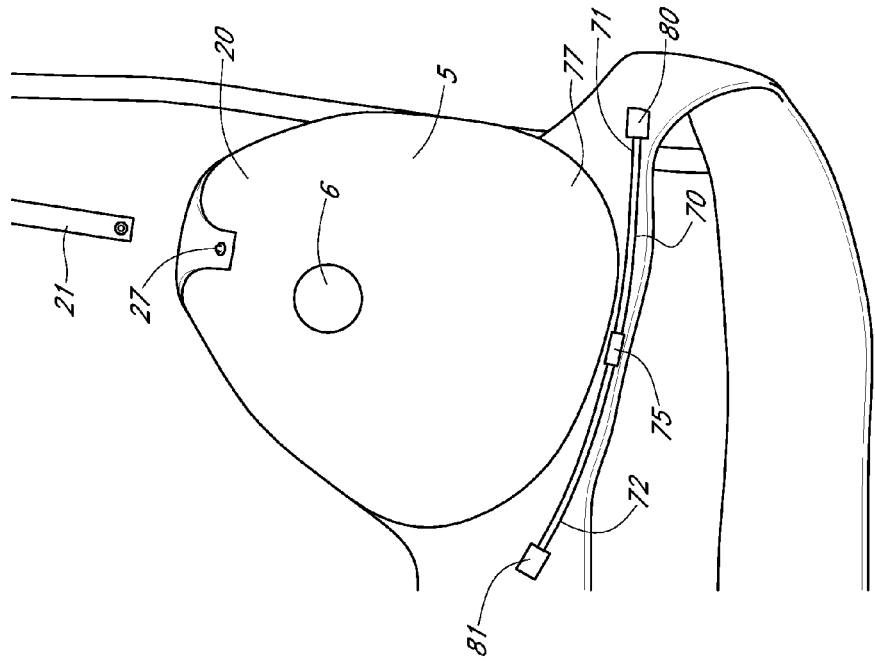
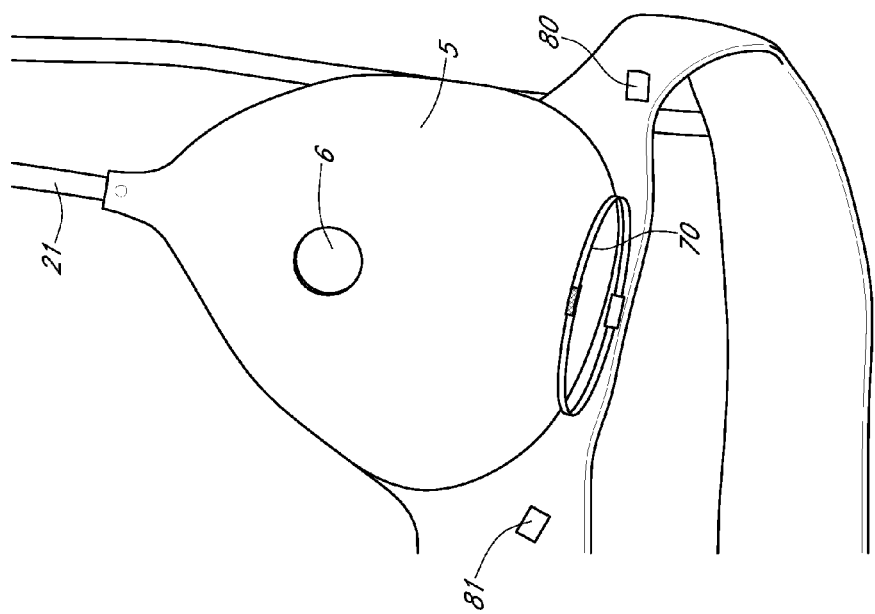

BRASSIERE CONFIGURED TO RECEIVE BREAST PUMP RECEPTACLE

FIELD OF THE INVENTION

The present invention relates to a bra, more specifically but not by way of limitation, a bra configured to receive and support the conical shaped breast shield and the milk receptacle of a breast pump so as to allow the user to substantially reduce their requirement to hold the breast pump components with their hands during the pumping process.

BACKGROUND

After giving birth to a child, the woman's breast begin to lactate within a few days producing breast milk. Breast milk is a superior nutritional food source for an infant when compared to artificial baby food. Millions of women breast feed their infants for up to one year in order to provide their infant with antibodies and proteins such as but not limited to lactoferrin. A healthy lactating woman secretes approximately 500 to 700 milliliters of milk per day. This amount of fluid can exceed the daily intake of an infant. As the nursing woman must continually express the milk in order to maintain the lactation process many women will use a breast pump to express and capture the milk for subsequent consumption by the child.

One issue with utilizing a breast pump is that is requires at least one hand of the nursing woman to manipulate and hold the pump during the pumping process. Most conventional breast pumps have a conical shaped breast shield that is superposed the breast and positioned such that the center of the conical breast shield is generally aligned with the areola of the breast. When a woman wishes to pump milk from a breast, she typically must remove her bra in order to position the breast shield in the proper location. The breast shield is connected to a reservoir or bottle that is used to store the milk as the milk is expressed from the breast. During the pumping process the woman must hold the reservoir as it fills with fluid so as to maintain the breast pump components in the correct location to effectively express milk from the breast.

Currently there are no devices to assist the woman in holding the breast pump components in the proper position during the pumping process. While there are nursing bras that have cups with detachable portions allowing access to the breast, these conventional bras offer no method of providing assistance with the holding of the breast pump components in the proper position during the pumping process.

Accordingly, there is a need for a bra configured to provide access to the breast without the need for the complete removal thereof and wherein the bra is further configured to releasably secure breast pump components so as to substantially reduce the requirement for a nursing woman to hold the breast pump components utilizing their hands.

SUMMARY OF THE INVENTION

It is the object of the present invention to provide a bra that functions to provide access to the breast without the need for the removal of the bra so as to allow the woman to express milk.

Another object of the present invention is to provide a bra that functions to provide access to the breast that further includes an aperture centrally located in the cup so a portion of the breast shield of a breast pump can be journaled therethrough.

Yet another object of the present invention is to provide a bra that functions to releasably secure a conical shape breast shield adjacent to the breast and maintain its position without the need for additional support from the user's hands.

A further object of the present invention is to provide a bra that is further configured to have releasably secured thereto a reservoir component of a breast pump.

An additional object of the present invention is to provide a bra that is further configured to have releasably secured thereto a reservoir component of a breast pump wherein the bra is capable of maintaining the correct position of the reservoir with substantially no support from the user's hands.

Yet a further object of the present invention is to provide a bra that includes a removable absorbent layer centrally located on the internal surface of the cup of the bra.

Still another object of the present invention is to provide a bra that makes expressing milk more comfortable and easier to perform.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

FIG. 1 is a frontal view of an embodiment of the present invention; and

FIG. 2 is a rear view of the embodiment of the present invention; and

FIG. 3 is a detailed view of the left cup area of the present invention wherein the bottle support member is deployed; and FIG. 4 is a detailed view of the left cup area of the present invention wherein the bottle support member is stowed.

DETAILED DESCRIPTION

Figure 5:
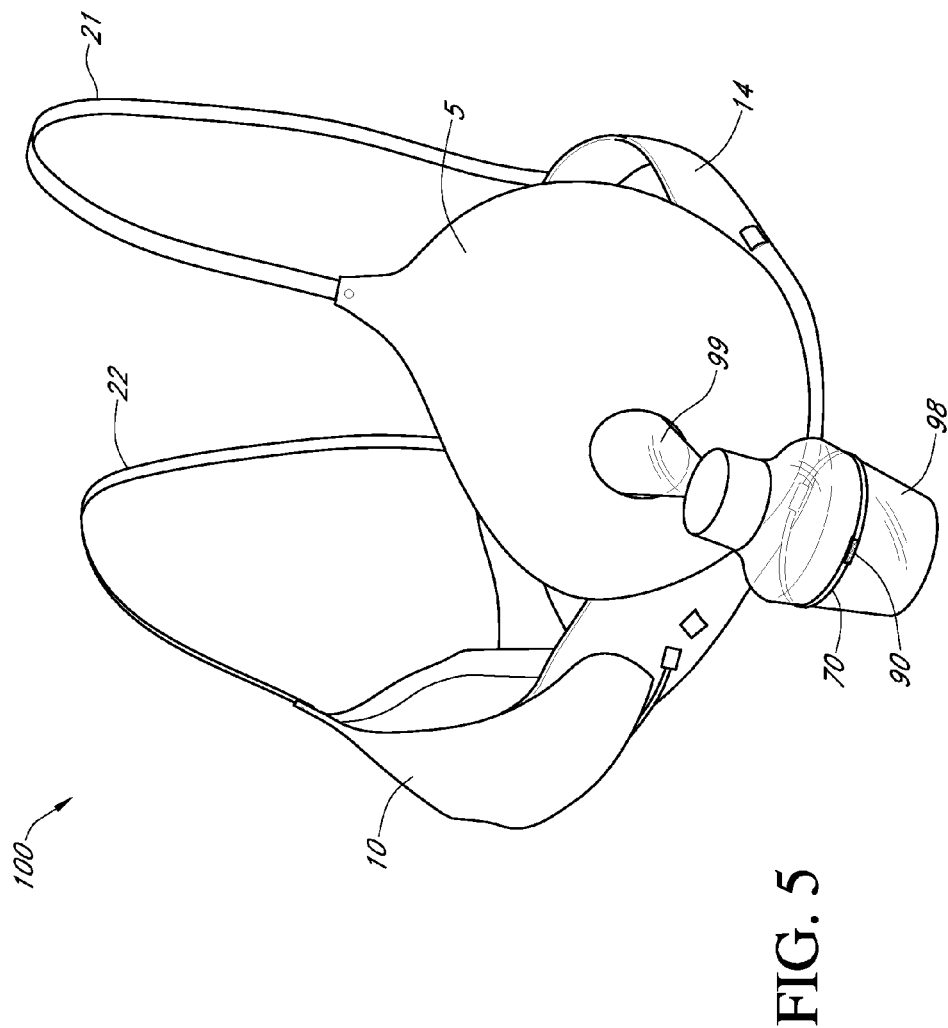
FIG. 5 is a perspective view of the embodiment of the present invention having a breast pump receptacle engaged therewith.

Referring now to the drawings submitted herewith, wherein various elements depicted therein are not necessarily drawn to scale and wherein through the views and figures like elements are referenced with identical reference numerals, there is illustrated a bra 100 constructed according to the principles of the present invention.

Referring now to FIGS. 1 and 2 the bra 100 further includes a left cup 5 and right cup 10 integrally formed with a stretchable strap 15 that is connected to the outside periphery 16, 18 of the left cup 5 and right cup 10 respectively. The stretchable strap 15 is secured utilizing a releasable fastener, not illustrated herein, distal to the left cup 5 and right cup 10. Shoulder straps 21, 22 are a secured proximate the top 20 of the left cup 5 and right cup 10 and extend to the rear portion 14 of the stretchable strap 15.

The stretchable strap 15 is manufactured from a suitable durable resilient material such as but not limited to nylon or woven cotton. The stretchable strap 15 functions to encircle the torso of a user and releasably secure the bra 100 to the torso of the user. While not illustrated herein it is contemplated within the scope of the present invention that the stretchable strap 15 is releasably secured utilizing a conventional fastener or hook proximate the rear portion 14. The conventional fastener functions to facilitate the placement or removal of the bra 100 on the torso of a user such that the stretchable strap 15 circumferentially surrounds the torso of the user when operably coupled thereto. Integrally secured to the stretchable strap 15 proximate the rear portion 14 are the shoulder straps 21, 22. The shoulder straps 21,22 function to further secure the bra 100 to the torso of the user. The shoulder straps 21, 22 further include a first end 23 and a second end 24. The shoulder straps 21,22 are manufactured from a suitable durable material such as but not limited to nylon or cotton and are integrally secured to the rear portion 14 of the stretchable strap 15 utilizing suitable methods such as but not limited to stitching. While the shoulder straps 21,22 illustrated herein are illustrated as being relatively thin in width, it is contemplated within the scope of the present invention that the shoulder straps 21,22 could be manufactured in numerous different widths. Furthermore, while the preferred embodiment illustrated herein utilizes two shoulder straps 21,22 to provide support for securing the bra 100 to the torso of a user, it is additionally contemplated within the scope of the present invention that the bra 100 could utilize only one shoulder strap or no shoulder straps and still achieve the desired functionality as described herein.

The left cup 5 and right cup 10 are manufactured from a suitable soft supportive material such as but not limited to cotton. The left cup 5 and right cup 10 are integrally secured to the stretchable strap 15 proximate the periphery 16 of the left cup 5 and periphery 18 of the right cup 10 utilizing suitable durable methods. The left cup 5 and right cup 10 are formed in a manner consistent with conventional bra cups and are manufactured in a variety of sizes. Centrally located within the left cup 5 is a first aperture 6. The first aperture 6 is generally annular in shape and is centrally located on the left cup 5 so as to substantially align with the areola and nipple area of a woman's breast. While the first aperture 6 is illustrated in its preferred embodiment herein as being generally annular in shape, it is contemplated within the scope of the present invention that the first aperture 6 could be formed in numerous different shapes and still permit substantial exposure of the areola and nipple area of a woman's breast. It is further contemplated within the scope of the present invention that the first aperture 6 could be manufactured in numerous different sizes. The first aperture 6 functions to allow the conical shaped portion of a conventional breast pump receptacle 98 to be engaged with a breast as the user has the bra 100 secured to their torso. The first aperture 6 permits the tube 99 of the breast pump receptacle to extend therethrough allowing the extraction of milk from the breast without the need for removal of the bra 100. Disposed on the interior surface 4 of the left cup 5 is a first pocket 40 and a second pocket 45. The first pocket 40 and second pocket 45 are located on opposing sides of the first aperture 6. The first pocket 40 and second pocket 45 are generally semi-annular in shape and are constructed so as to form an interior volume configured to receive the absorbent pad 50. The absorbent pad 50 is illustrated herein in FIG. 2 being placed in its first position on the right cup 10. While the absorbent pad 50 is only illustrated herein on the right cup 10 it is contemplated within the scope of the present invention that an absorbent pad 50 is also placed within the left cup 5 so as to substantially cover the first aperture 6. The absorbent pad 50 is manufactured in a generally annular material and is constructed in a thin manner and from an absorbent material so subsequent being placed in its first position such that the absorbent pad 50 is substantially covering the first aperture 6, the absorbent pad 50 functions to capture any lactation leakage that occurs from the nipple either prior to or subsequent nursing or milk extraction utilizing a breast pump. It is contemplated within the scope of the present invention that the absorbent pad 50 is manufactured such that its thickness does not interfere with the appearance of the clothing that is superposed the bra 100. Those skilled in the art should recognize that the first pocket 40 and second pocket 45 could be formed in numerous different shapes and located in various positions circumferentially around the first aperture 6 and still achieve the desired function as described herein. Additionally, while good results have been achieved utilizing a first pocket 40 and second pocket 45 as shown and described herein to facilitate the securing of the absorbent pad 50, it is further contemplated within the scope of the present invention that the absorbent pad 50 could be secured to the interior surface 4 utilizing numerous suitable fastening methods such as but not limited to hook and loop fasteners.

As shown in particular in FIG. 4, the left cup 5 is releasably secured proximate the top 20 to the shoulder strap 22 utilizing fastener 27. The left cup 5 is releasably secured to the shoulder strap 22 so as to facilitate the folding of the left cup 5 in a generally downward direction towards the bottom edge 77 so the breast disposed therein can be exposed and the conical portion of a breast pump receptacle can be superposed the nipple and areola. Subsequent the conical portion of a conventional breast pump receptacle being superposed the areola and nipple of the breast, the left cup 5 is returned to its first position wherein the top 20 is releasably secured to the should strap 21 utilizing the fastener 27 and the tube 99 is journaled through the first aperture 6.

Referring in particular to FIGS. 4 and 5, the bra 100 further includes a bottle support member 70. The bottle support member 70 is generally elongated in shape and is constructed of a suitable durable resilient material such as but not limited to metal. The bottle support member 70 includes a first end 71 and a second end 72 that are positioned in a first slot 80 and second slot 81 respectively when the bottle support member 70 is not circumferentially mounted to a conventional breast pump receptacle. The bottle support member 70 is secured at its midpoint 75 to the conventional underwire (not illustrated herein) that is typically present underneath the cups of a conventional bra to provide support. The bottle support member 70 is secured to the conventional underwire utilizing suitable durable methods. As shown in particular in FIG. 5, the bottle support member 70 functions to circumferentially surround a conventional breast pump receptacle 98 and provide substantial support thereof such that the user can extract milk without the need for additional support of the breast pump receptacle 98. This allows the user to perform other tasks with their hands during the extraction of the milk form their breasts. The first end 71 and second end 72 are configured with mateable fasteners 90 so as to secure the bottle support member 70 securely around the breast pump receptacle 98. It is contemplated within the scope of the present invention that the fasteners 90 could be manufactured from numerous suitable conventional fasteners such as but not limited to hook and loop fasteners.

The bra 100 further includes a second bottle support member 170 secured generally underneath the right cup 10 and is manufactured in the same manner as the bottle support member 70 wherein the second bottle support member 170 has a first end 171 and second end 172 that are disposed within the slots 180,181 respectively when the bottle support member 170 is not engaged with a conventional breast pump receptacle. The second bottle support member 170 functions in the same manner to support a conventional breast pump receptacle as described herein for the bottle support member 70.

Additionally, the right cup 10 is constructed in an identical manner as the left cup 5 as described herein. The right cup 10 includes an aperture 66 and is configured to be releasably secured to shoulder strap 22 utilizing an attachment mechanism 37. The right cup 10 further includes a first pocket 140 and second pocket 145 manufactured identical in manner as the first pocket 40 and second pocket 45 as described herein. It is contemplated within the scope of the present invention that the right cup 10 is constructed identical in manner and includes all of the elements of the left cup 5 as described and illustrated herein.

Referring in particular to FIGS. 4 and 5, a description of the operation is as follows. In use, upon a user desiring to extract milk from at least one of their breast, for exemplary purposes the user's left breast, while the user is engaged with the bra 100, the user will release the top portion 20 of the left cup 5 utilizing the fastener 27 so as to fold the left cup 5 in a downward direction so as to substantially expose the breast. The user places the conical shaped portion of a conventional breast pump receptacle over the areola and nipple area of the breast and returns the top portion 20 proximate the shoulder strap 21 and secures thereto utilizing the fastener 27. The first aperture 6 permits the tube 99 to be journaled therethrough so that it can be operably connected to the breast pump receptacle 98. Subsequent the user operably coupling the breast pump receptacle 98 to the tube 99, the user deploys the bottle support member 70 by removing the first end 71 and second end 72 from first slot 80 and second slot 81 respectively. The bottle support member 70 is then circumferentially disposed around the breast pump receptacle 98 such that the first end 71 and second end 72 are proximate to each other and secured utilizing fastener 90. Ensuing the circumferential mounting of the bottle support member 70 to the breast pump receptacle 98, the breast pump receptacle is supported such that not other substantial support device or assistance from the user is required during the milk extraction process. Following the extraction of the desired amount of milk from the breast, the bottle support member 70 is returned to its first position and the conical shape portion of the conventional breast pump receptacle is removed and the absorbent pad 50 is secured adjacent to and substantially covering the first aperture utilizing the first pocket 40 and second pocket 45.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A bra comprising:
    a pair of bra cups, said pair of bra cups having a concave interior surface, said bra cups having an aperture, said aperture being centrally located on each of said bra cups, said bra cups having an upper portion and a lower portion, said bra cups being releasably secured to the bra proximate said upper portion;
    a strap, said strap being integrally formed with said bra cups, said strap configured to circumferentially secure the bra to the torso of a user;
    a first bottle support member, said first bottle support member being secured to said strap generally underneath a first of one of said bra cups, said first bottle support member having a first position and a second position, said first bottle support member configured to be releasably secured to a breast pump milk receptacle in said second position; and
    wherein said apertures of said bra cups are generally aligned with the areola and nipple area of a breast disposed within said bra cups so as to facilitate the connection of a conical shaped portion of a conventional breast pump.

2. The bra as recited in claim 1, and further including a second bottle support member, said second bottle support member being secured to said strap generally underneath a second one of said bra cups, said second bottle support member having a first position and a second position, said second bottle support member configured to be releasably secured to a breast pump milk receptacle placed adjacent the breast and provide support therefore in said second position.

3. The bra as recited in claim 2, and further including a first absorbent pad and a second absorbent pad, said first absorbent pad and said second absorbent pad being removably attached to said pair of bra cups, said first absorbent pad and said second absorbent pad operable to substantially cover said apertures of said bra cups.

4. The bra as recited in claim 3, wherein said bra cups further a first pocket and a second pocket, said first pocket being formed within a first of said pair of bra cups, said second pocket being formed within a second of said pair of bra cups, said first pocket and said second pocket operable to receive said first absorbent pad and said second absorbent pad so as to substantially cover said apertures of said pair of bra cups.

5. The bra as recited in claim 4, wherein said first bottle support member and said second bottle support member have a first end and a second end, said first end and said second end configured to be connectable so as to form a ring, said first bottle support member and said second bottle support member further configured to be resilient.

6. The bra as recited in claim 5, wherein said first bottle support member and said second bottle support member are generally linear in manner and against said strap in said first position.

7. A bra operable to provide assistance to a user in supporting at least a portion of a breast pump milk receptacle comprising:
    a strap, said strap being generally stretchable so as to circumferentially surround a user's torso, said strap further including at least one fastener, said strap configured to releasably secure the bra to a user's torso;
    a first bra cup, said first bra cup being integrally formed with said strap, said first bra cup having a concave interior surface, said first bra cup having an upper portion and a lower portion, said first bra cup being releasably secured proximate said upper portion, said first bra cup having an aperture, said aperture being centrally located on said first bra cup, said aperture being in general alignment with the areola and nipple of a breast disposed within said first bra cup;
    a second bra cup, said second bra cup being integrally formed with said strap, said second bra cup having a concave interior surface, said second bra cup having an upper portion and a lower portion, said second bra cup being releasably secured proximate said upper portion, said second bra cup having an aperture, said aperture being centrally located on said second bra cup, said aperture being in general alignment with the areola and nipple of a breast disposed within said second bra cup; and wherein said apertures of said first bra cup and said second bra cup are operable to have journaled therethrough at least a portion of a tube of a conical shaped portion of a conventional breast pump so as to assist in the facilitation of holding the conical shaped portion of the breast pump adjacent to the breast disposed within either said first cup or said second cup.

8. The bra as recited in claim 7, wherein said first bra cup further includes a first absorbent pad, said first absorbent pad being releasably secured to said first bra cup, said first absorbent pad being generally annular in shape, said first absorbent pad operable to cover said aperture of said first bra cup.

9. The bra as recited in claim 8, wherein said second bra cup further includes a second absorbent pad, said second absorbent pad being releasably secured to said second bra cup, said second absorbent pad being generally annular in shape, said second absorbent pad operable to cover said aperture of said second bra cup.

10. The bra as recited in claim 9, and further including a first bottle support member, said first bottle support member secured to said strap underneath said first bra cup, said first bottle support member being generally elongated in shape, said first bottle support member having a first end and a second end, said first end and said second end operable to be releasably secured so as to form a ring underneath said first bra cup.

11. The bra as recited in claim 10, and further including a second bottle support member, said second bottle support member secured to said strap underneath said second bra cup, said second bottle support member being generally elongated in shape, said second bottle support member having a first end and a second end, said first end and said second end of said second bottle support member operable to be releasably secured so as to form a ring underneath said second bra cup.

12. The bra as recited in claim 11, wherein said first bottle support member is configured to be movable to a second position, said first bottle support member being ring-shaped in said second position, said first end and said second end of said first bottle support member being releasably secured upon said first bottle support member being placed in said second position, said first bottle support member operable to provide support for a breast pump milk receptacle in said second position.

13. The bra as recited in claim 12, wherein said second bottle support member is configured to be movable to a second position, said second bottle support member being ring-shaped in said second position, said first end and said second end of said second bottle support member being releasably secured upon said second bottle support member being placed in said second position, said second bottle support member operable to provide support for a breast pump milk receptacle in said second position.

14. A bra operable to receive the conical portion of a conventional breast pump such that the conical portion of the conventional breast pump is intermediate the breast disposed within the bra and the bra cup and wherein the bra is operable to support a milk receptacle coupled to the conical portion of the conventional breast pump so as to facilitate support thereof during the milk extraction process comprising:

a stretchable strap, said stretchable strap operable to circumferentially surround a user's torso, said stretchable strap further including a fastener, said strap configured to releasably secure the bra to a user's torso;

a left bra cup, said left bra cup being integrally formed with said stretchable strap, said left bra cup having a concave interior surface, said left bra cup having an upper portion and a lower portion, said left bra cup further including a lower peripheral edge, said left bra cup being releasably secured proximate said upper portion, said left bra cup operable to be folded down towards said lower peripheral edge so as to expose the breast of the user, said left bra cup having an aperture, said aperture being generally annular in shape, said aperture being centrally located on said left bra cup, said aperture being in general alignment with the areola and nipple of a breast disposed within said left bra cup upon said left bra cup being secured proximate said upper portion;

a right bra cup, said right bra cup being integrally formed with said stretchable strap, said right bra cup having a concave interior surface, said right bra cup having an upper portion and a lower portion, said right bra cup further including a lower peripheral edge, said right bra cup being releasably secured proximate said upper portion, said right bra cup operable to be folded towards said lower peripheral edge so as to expose the breast of the user disposed therein, said right bra cup having an aperture, said aperture being centrally located on said right bra cup, said aperture being generally annular in shape, said aperture being in general alignment with the areola and nipple of a breast disposed within said right bra cup upon said right bra cup being secured proximate said upper portion; and wherein said left bra cup and said right bra cup are operable to releasably secure the conical shaped portion of a breast pump adjacent to the user's breast disposed within said left bra cup and said right bra cup and wherein said aperture is operable to have journaled therethrough at least a portion of the conical shaped portion of the conventional breast pump.

15. The bra as recited in claim 14, wherein said left cup further includes a first absorbent pad, said first absorbent pad configured to be removable, said first absorbent pad generally thin in manner and annular in shape, said first absorbent pad operable to cover said aperture of said left cup.

16. The bra as recited in claim 15, wherein said right cup further includes a second absorbent pad, said second absorbent pad configured to be removable, said second absorbent pad generally thin in manner and annular in shape, said second absorbent pad operable to cover said aperture of said right cup.

17. The bra as recited in claim 16, and further including a first bottle support member, said first bottle support member secured to said stretchable strap proximate the midpoint of said first bottle support member underneath said left cup, said first bottle support member being generally elongated in shape and resilient in manner, said first bottle support member having a first end and a second end, said first end and said second end releasably secured proximate said strap, said first end of said first bottle support member being releasably secured in a first slot, said first slot integrally formed with said stretchable strap, said first slot operable to maintain said first end generally adjacent said stretchable strap, said second end of said first bottle support member releasably secured in a second slot, said second slot integrally formed with said stretchable strap, said second slot operable to maintain said second end generally adjacent said stretchable strap, said first bottle support member having a first position and a second position, said first bottle support member being generally planar in manner and adjacent said stretchable strap in said first position, said first bottle support member being generally loop shaped extending perpendicular from said stretchable strap, said first bottle support member operable to support a milk receptacle of a conventional breast pump in said second position.

18. The bra as recited in claim 17, and further including a second bottle support member, said second bottle support member secured to said stretchable strap proximate the midpoint of said second bottle support member underneath said right cup, said second bottle support member being generally elongated in shape and resilient in manner, said second bottle support member having a first end and a second end, said first end and said second end releasably secured proximate said stretchable strap, said first end of said second bottle support member being releasably secured in a third slot, said third slot integrally formed with said stretchable strap, said third slot operable to maintain said first end generally adjacent said stretchable strap, said second end of said second bottle support member releasably secured in a fourth slot, said fourth slot operable to maintain said second end generally adjacent said stretchable strap, said second bottle support member having a first position and a second position, said second bottle support member being generally planar in manner and adjacent said stretchable strap in said first position, said second bottle support member being generally loop shaped extending perpendicular from said stretchable strap, said second bottle support member operable to support a milk receptacle of a conventional breast pump in said second position.

19. The bra as recited in claim 18, wherein said left bra cup and said right bra cup further include a pair of pockets, said pair of pockets being adjacent said apertures, said pair of pockets configured to releasably secure said first absorbent pad and said second absorbent pad so as to substantially cover said apertures.

\* \* \* \* \*